United States Patent
Thakur et al.

(10) Patent No.: US 11,077,428 B2
(45) Date of Patent: *Aug. 3, 2021

(54) HYDROGENOLYSIS CATALYSTS WITH HIGH ACID TOLERANCE

(71) Applicant: BASF Corporation, Florham Park, NJ (US)

(72) Inventors: Deepak S. Thakur, Solon, OH (US); William O. Tuttle, Cleveland Heights, OH (US); Arunabha Kundu, Richmond Heights, OH (US); Keenan Lee Deutsch, Iselin, NJ (US); Jeffrey Baciak, Brook Park, OH (US)

(73) Assignee: BASF Corporation, Florham Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/511,289

(22) Filed: Jul. 15, 2019

(65) Prior Publication Data

US 2019/0336944 A1    Nov. 7, 2019

Related U.S. Application Data

(63) Continuation of application No. 15/561,220, filed as application No. PCT/US2016/024159 on Mar. 25, 2016, now Pat. No. 10,350,577.
(Continued)

(51) Int. Cl.
*B01J 21/04* (2006.01)
*B01J 21/08* (2006.01)
(Continued)

(52) U.S. Cl.
CPC ............ *B01J 23/002* (2013.01); *B01J 21/14* (2013.01); *B01J 23/72* (2013.01); *B01J 23/80* (2013.01);
(Continued)

(58) Field of Classification Search
CPC ...... B01J 21/12; B01J 35/002; B01J 35/0026; B01J 35/0066; B01J 35/1014;
(Continued)

(56) References Cited

U.S. PATENT DOCUMENTS 2,750,263 A    6/1956 De Nora et al.
4,257,874 A    3/1981 Bergna
(Continued)

FOREIGN PATENT DOCUMENTS

CN    102476056 A    5/2012
JP    55-031428 A    3/1980
(Continued)

OTHER PUBLICATIONS

Communication Pursuant to Rule 114(2) in EP Application No. 16769750.7, dated Mar. 7, 2019 (8 pages).
(Continued)

*Primary Examiner* — Cam N. Nguyen
(74) *Attorney, Agent, or Firm* — Lowenstein Sandler LLP

(57) ABSTRACT

A catalyst includes a mixed metal oxide; an alumina; silica, and calcium, where the mixed metal oxide includes Cu and at least one of Mn, Zn, Ni, or Co. Such catalysts exhibit enhanced tolerance sulfur-containing compounds and free fatty acids.

15 Claims, 3 Drawing Sheets

Related U.S. Application Data

(60) Provisional application No. 62/138,854, filed on Mar. 26, 2015.

(51) Int. Cl.

| | | |
|---|---|---|
| *B01J 21/12* | (2006.01) | |
| *B01J 23/00* | (2006.01) | |
| *B01J 23/72* | (2006.01) | |
| *B01J 23/78* | (2006.01) | |
| *B01J 23/80* | (2006.01) | |
| *B01J 23/88* | (2006.01) | |
| *B01J 35/10* | (2006.01) | |
| *B01J 37/00* | (2006.01) | |
| *B01J 37/04* | (2006.01) | |
| *B01J 37/08* | (2006.01) | |
| *C07C 29/149* | (2006.01) | |
| *B01J 23/889* | (2006.01) | |
| *B01J 35/00* | (2006.01) | |
| *B01J 21/14* | (2006.01) | |
| *B01J 23/70* | (2006.01) | |

(52) U.S. Cl.
CPC ....... *B01J 23/8892* (2013.01); *B01J 35/0066* (2013.01); *B01J 35/1014* (2013.01); *B01J 35/1038* (2013.01); *B01J 35/1042* (2013.01); *B01J 37/0018* (2013.01); *B01J 37/04* (2013.01); *B01J 37/08* (2013.01); *C07C 29/149* (2013.01); *B01J 23/70* (2013.01); *B01J 35/002* (2013.01); *B01J 35/0026* (2013.01); *B01J 2231/60* (2013.01); *B01J 2523/00* (2013.01); *B01J 2523/23* (2013.01); *B01J 2523/27* (2013.01); *B01J 2523/72* (2013.01); *B01J 2523/845* (2013.01); *B01J 2523/847* (2013.01)

(58) Field of Classification Search
CPC .... B01J 35/1038; B01J 35/1042; B01J 23/72; B01J 23/78; B01J 23/80; B01J 23/84; B01J 23/8892; B01J 21/04; B01J 21/08; B01J 23/002; B01J 35/1019; B01J 37/0018; B01J 37/04; B01J 37/08; C07C 29/149

See application file for complete search history.

(56) References Cited

U.S. PATENT DOCUMENTS

| | | |
|---|---|---|
| 4,272,409 A | 6/1981 | Bergna |
| 5,138,106 A | 8/1992 | Wilmott et al. |
| 5,157,168 A | 10/1992 | Wilmott et al. |
| 5,406,004 A | 4/1995 | Eastland et al. |
| 5,478,789 A | 12/1995 | Hattori et al. |
| 5,977,010 A * | 11/1999 | Roberts .............. B01J 21/16 502/244 |
| 5,997,010 A | 12/1999 | Lloyd |
| 6,049,008 A | 4/2000 | Roberts et al. |
| 6,596,667 B2 | 7/2003 | Bellussi et al. |
| 7,022,645 B2 | 4/2006 | Ryu et al. |
| 8,293,676 B2 | 10/2012 | King et al. |
| 8,450,234 B2 * | 5/2013 | Baek .............. B01J 23/825 502/201 |
| 9,029,286 B2 | 5/2015 | Neltner et al. |
| 9,700,874 B2 * | 7/2017 | Bartek .............. C10G 1/08 |
| 2010/0056364 A1 | 3/2010 | Huber-Dirr et al. |
| 2012/0130101 A1 | 5/2012 | Yoo et al. |
| 2012/0136179 A1 | 5/2012 | Thakur et al. |
| 2013/0079568 A1 | 3/2013 | Partridge et al. |

FOREIGN PATENT DOCUMENTS

| | | |
|---|---|---|
| JP | H08-108072 A | 4/1996 |
| WO | WO-91/04789 A1 | 4/1991 |
| WO | WO-97/34694 A1 | 9/1997 |
| WO | WO-2009/044210 A1 | 4/2009 |
| WO | WO-2012/043905 A1 | 4/2012 |

OTHER PUBLICATIONS

Extended European Search Report in EP Application No. 16769750. 7, dated Sep. 24, 2018 (10 pages).

He et al., "Effect of structure of CuO/ZnO/Al2O3 composites on catalytic performance for hydrogenation of fatty acid ester," Applied Catalysis A: General, 2013, vol. 452, pp. 88-93.

International Search Report and Written Opinion in International Application No. PCT/US2016/024159, dated Jul. 25, 2016 (11 pages).

Notice of Allowance in U.S. Appl. No. 15/561,220, dated Mar. 7, 2019 (10 pages).

Evans, et al. "On the determination of copper surface area by reaction with nitrous oxide," Applied Catalysis, 7(1):75-83 (1983). Abstract Only.

* cited by examiner

HYDROGENOLYSIS CATALYSTS WITH HIGH ACID TOLERANCE

CROSS-REFERENCE TO RELATED APPLICATIONS

This application is a continuation of U.S. patent application Ser. No. 15/561,220, filed on Sep. 25, 2017, now U.S. Pat. No. 10,350,577, which is a U.S. National Phase Application under 35 U.S.C. § 371 of International Application No. PCT/US2016/024159, filed on Mar. 25, 2016, which claims benefit of priority to U.S. Provisional Application No. 62/138,854, filed on Mar. 26, 2015, the entire contents of which are incorporated herein by reference in their entireties.

FIELD

The present technology relates generally to the field of hydrogenolysis and/or hydrogenation of feedstocks, wherein the feedstock includes at least one carbonyl group. More specifically, the catalysts of the present technology are highly active for the hydrogenolysis of fatty acid methyl esters to produce fatty alcohols. The present technology provides catalysts that exhibit remarkable acid impurity tolerance as well as methods of making the catalysts and processes involving the catalysts.

BACKGROUND

Current commercial catalysts for hydrogenolysis of fatty acid esters utilize CuCr tablets. These catalysts are activated with hydrogen to reduce the CuO to form what is commonly believed to be the active site. Without being bound by theory, it is believed the active site involves $Cu^o$. The feed for producing fatty alcohols may contain impurities, such as, but not limited to, sulfur or free fatty acids (FFAs). Sulfur can poison $Cu^o$ active sites in the catalyst, thereby deactivating the catalyst. FFAs may compete for adsorption sites where ester hydrogenolysis takes place, thereby significantly inhibiting the rate of ester hydrogenolysis (a reversible deactivation). FFAs may also accelerate the $Cu^o$ crystallite growth thereby causing activity loss (a permanent deactivation). The main causes of catalyst deactivation are: copper crystallite growth, sulfur, and coke deposition.

SUMMARY

In one aspect, a catalyst is provided that includes a mixed metal oxide, alumina; silica; and calcium, where the mixed metal oxide includes Cu and at least one of Mn, Zn, Ni, or Co. In some embodiments, the copper dispersion of the activated catalyst is from about 0.5% to about 20%.

In some embodiments, the catalyst includes about 15 wt % to about 50 wt % Cu. In some embodiments, the mixed metal oxide includes Cu and Mn. In some embodiments, the mixed metal oxide includes Cu and Mn, and the catalyst includes about 2 wt % to about 10 wt % Mn. In some embodiments, the mixed metal oxide includes Cu and Zn. In some embodiments, the mixed metal oxide includes Cu and Zn, and the catalyst includes about 15 wt % to about 50 wt % Zn.

In some embodiments, the amount of the alumina in the catalyst is from about 10 wt % to about 30 wt %. In some embodiments, the amount of the silica in the catalyst is from about 10 wt % to about 30 wt %. In some embodiments, the amount of the calcium in the catalyst is from about 2 wt % to about 10 wt %. In some embodiments, the catalyst is substantially free of sodium. In some embodiments, the catalyst is substantially free of chromium. In some embodiments, the catalyst is substantially free of barium.

In some embodiments, the catalyst has a Brunauer-Emmett-Teller surface area from about 10 $m^2/g$ to about 150 $m^2/g$. In some embodiments, the catalyst has a Brunauer-Emmett-Teller surface area from about 10 $m^2/g$ to about 70 $m^2/g$. In some embodiments, the catalyst has a mercury pore volume from about 0.10 $cm^3/g$ to about 0.80 $cm^3/g$. In some embodiments, the catalyst has a packed ambient bulk density from about 0.3 $g/cm^3$ to about 1.6 $g/cm^3$. In some embodiments, the catalyst has a side crush strength from about 2.5 lbs/mm to about 12 lbs/mm.

In some embodiments, the catalyst is in a shape includes at least one of cylindrical, tubular, polylobular, fluted, or ridged. In some embodiments, the catalyst has a diameter from about 0.5 mm to about 3.0 mm. In some embodiments, the diameter is from about 1.0 mm to about 2.0 mm.

In an aspect, a method of making the catalyst of any of the above embodiments is provided where the method includes calcining a shaped material. The shaped material is formed by shaping a paste, the paste including a Cu oxide and at least one metal oxide of Mn, Zn, Ni, or Co; an alumina; a silica sol; and calcium hydroxide. In some embodiments, the paste further includes a solvent. In some embodiments, the paste further includes a clay material. In some embodiments, the shaped material is prepared by tableting or extruding the paste. In some embodiments, the paste further includes an extrusion aid. In some embodiments, the extrusion aid includes a polysaccharide. In some embodiments, the Cu oxide includes cupric oxide. In some embodiments, the calcining comprises a temperature from about 300° C. to about 1,000° C. In some embodiments, the duration of the calcining step is about 15 minutes to about 12 hours. In some embodiments, the shaped material is dried prior to calcining. In some embodiments, the shaped material is dried at a temperature from about 40° C. to about 250° C.

In an aspect, process is provided where the process involves hydrogenating a feedstock by contacting the feedstock and $H_2$ with the catalyst of any one of the above described embodiments, wherein the feedstock includes at least one carbonyl group. In some embodiments, the feedstock includes compounds where the longest carbon chain has a carbon number from $C_8$-$C_{18}$. In some embodiments, the feedstock includes fatty acid methyl esters. In some embodiments, the feedstock includes free fatty acids.

DETAILED DESCRIPTION

Figure 1:
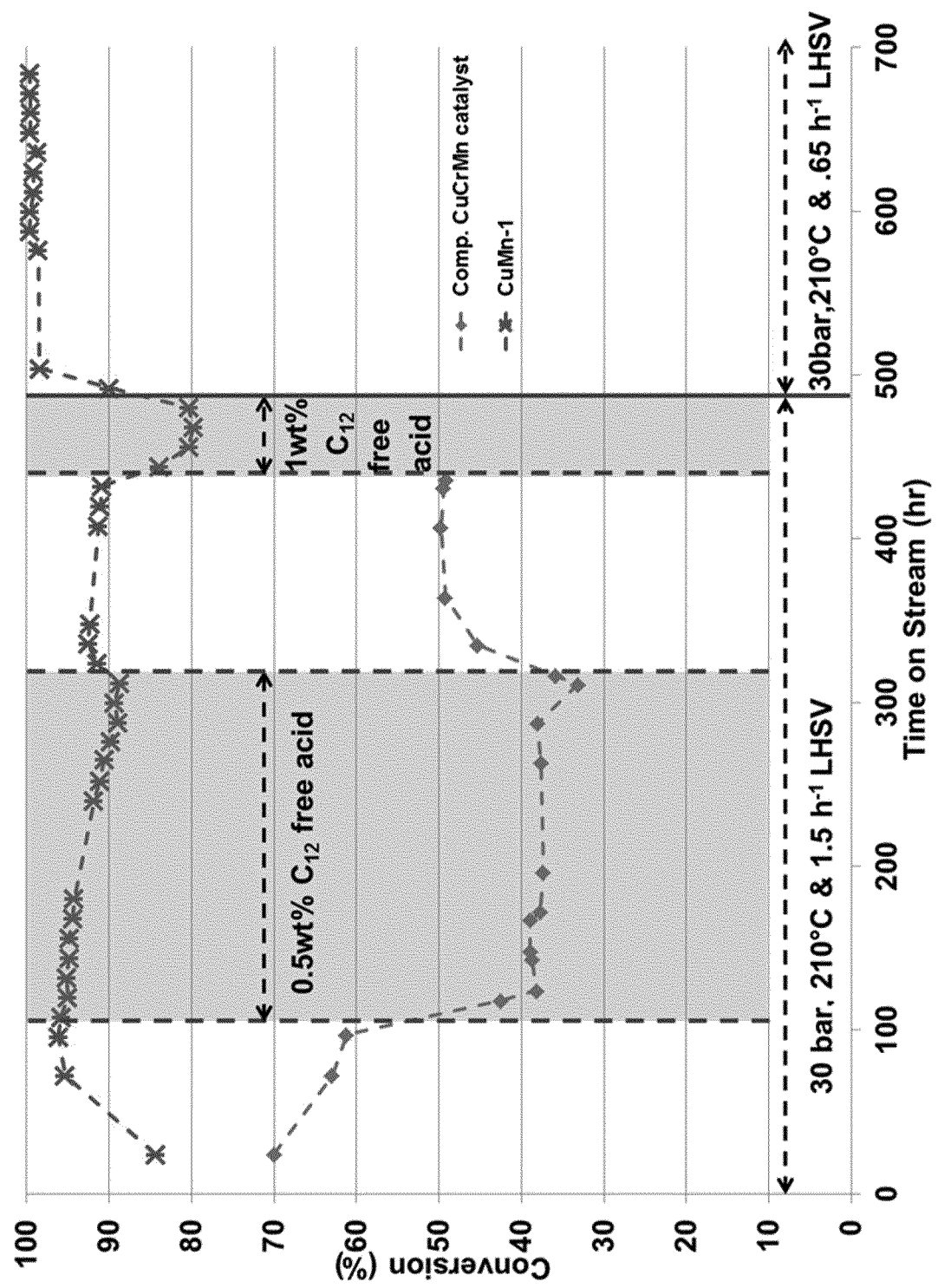
FIG. 1 illustrates the hydrogenolysis performance of one embodiment of a catalyst of the present technology for a $C_{12}$-$C_{14}$ fatty acid methyl ester ($C_{12}$-$C_{14}$ FAME) feed in comparison to a CuCrMn catalyst, according to the working examples.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

"Substantially free" as used herein will be understood by persons of ordinary skill in the art and will vary to some extent depending upon the context. If there are uses of the term which are not clear to persons of ordinary skill in the art, given the context in which it is used, "substantially free" will mean that the substance is at about 0.5 wt % or less.

Fatty alcohols, also commonly referred to as detergent alcohols, are chemical intermediates used in the oleochemical industry for manufacturing detergents, cosmetics, and industrial waxes. The fatty alcohols are monohydric aliphatic alcohols of 6 to 34 atoms. They may be produced by oleochemical routes that involve hydrogenolysis of esters of palm or coconut oils to alcohols, petrochemical processes that involve oligomerization, and/or hydroformylation followed by oxo-aldehyde hydrogenation to alcohols. Fatty alcohols may also be made from petrochemical feed stocks.

Catalysts have been identified, and are described herein, that, when used in a hydrogenation and/or hydrogenolysis reaction to produce fatty alcohols, exhibit high tolerance to sulfur and FFAs. The catalyst may be converted to other, more active catalytic species, either prior to a catalyzed reaction, or during the course of a catalyzed reaction by contacting the catalyst with $H_2$ at about 150° C. to about 250° C. For example, while copper oxide possesses some hydrogenolysis activity, during the course of a hydrogenolysis reaction converting a Cu fatty acid ester to dodecanol under hydrogen pressure it may be that at least some copper oxide is converted to a species more active in the hydrogenolysis of the Cu fatty acid ester. For example, and without being bound by theory, it is believed that the more active species in hydrogenation and hydrogenolysis involves $Cu^{\circ}$. Such a reduction to provide a portion of the composition with a more catalytically active component may also be carried out in advance of the hydrogenation and/or hydrogenolysis reaction by contacting the catalyst with $H_2$ prior to the hydrogenation and/or hydrogenolysis reaction.

The catalysts include a mixed metal oxide, alumina, silica, and calcium, where the mixed metal oxide includes Cu and at least one of Mn, Zn, Ni, or Co. The catalyst may include about 15 wt % to about 50 wt % Cu. The amount of Cu in the catalyst may be about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 47 wt %, about 48 wt %, about 49 wt %, about 50 wt % as well as any range including, and in between, any two of these values. For example, the catalyst may include about 26 wt % to about 40 wt % Cu.

As disclosed above, the mixed metal oxide also includes at least one of Mn, Zn, Ni, or Co. Thus, the mixed metal oxide may include Mn, Zn, Ni, Co, or a combination of any two or more thereof in addition to the Cu. The catalyst may include about 1 wt % to about 30 wt % of Mn, Zn, Ni, Co, or combination of any two or more thereof. The amount of Mn, Zn, Ni, or Co, or the combination of any two or more thereof in the catalyst, may be about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, or any range including and in between any two of these values.

In any of the above embodiments, the "copper dispersion" of the catalyst may be from about 0.5% to about 20%. "Copper dispersion" is defined as the ratio, commonly reported as percentage, of the Cu atoms accessible via gaseous diffusion of gas molecules such as $N_2O$ (i.e., surface exposed atoms) to total number of Cu atoms of the catalyst. This ratio represents the percent of Cu at the surface available to catalyze chemical reactions in relation to total bulk Cu content of the catalyst. The copper dispersion of any of the catalysts described herein may be about 0.5%, about 0.6%, about 0.7%, about 0.8%, about 0.9%, about 1.0%, about 1.2%, about 1.4%, about 1.6%, about 1.8%, about 2.0%, about 2.2%, about 2.4%, about 2.6%, about 2.8%, about 3.0%, about 3.2%, about 3.4%, about 3.6%, about 3.8%, about 4.0%, about 4.2%, about 4.4%, about 4.6%, about 4.8%, about 5.0%, about 5.2%, about 5.4%, about 5.6%, about 5.8%, about 6.0%, about 6.2%, about 6.4%, about 6.6%, about 6.8%, about 7.0%, about 7.2%, about 7.4%, about 7.6%, about 7.8%, about 8.0%, about 8.2%, about 8.4%, about 8.6%, about 8.8%, about 9.0%, about 9.2%, about 9.4%, about 9.6%, about 9.8%, about 10.0%, about 10.5%, about 11%, about 11.5%, about 12.0%, about 12.5%, about 13.0%, about 13.5%, about 14.0%, about 14.5%, about 15.0%, about 15.5%, about 16.0%, about 16.5%, about 17.0%, about 17.5%, about 18.0%, about 18.5%, about 19.0%, about 19.5%, about 20%, or any range including and in between any two of these values.

Methods of determining copper dispersion of a catalyst, include, but are not limited to, the methods described in Evans, J. W. et al. "On the Determination of Copper Surface Area by Reaction with Nitrous Oxide," *Applied Catalysis*, 1983, 7, 75-83; Amorim de Carvalho, M. C. N. et al. "Quantification of metallic area of high dispersed copper on ZSM-5 catalyst by TPD of $H_2$,'" *Catalysis Communications*, 2002, 3, 503-509; Sato, S. et al. "Distinction Between Surface and Bulk Oxidation of Cu through $N_2O$ Decomposition," *Journal of Catalysis*, 2000, 196, 195-199; Jensen, J. R. et al. "An Improved $N_2O$-method for measuring Cu-dispersion," *Applied Catalysis A*, 2004, 266, 117-122; and Gervasini, A., Gennici, S., "Dispersion and surface states of copper catalysts by temperature-programmed-reduction of oxidized surfaces (s-TPR)," *Applied Catalysis A*, 2005, 281, 199-205, each of which is incorporated herein by reference in its entirety for any and all purposes.

One procedure for determining Cu dispersion and Cu surface area is as follows: a calcined catalyst is reduced at 210° C. for 90 minutes after a 5° C./min ramp in 5% $H_2$/95% $N_2$ gas. The reduced catalyst is cooled to 60° C. and held at that temperature for 15 minutes while it is purged with He. At 60° C., 2% $N_2O$/98% He is passed over the reduced catalyst and the evolution of $N_2$ is observed by a thermal conductivity detector in conjunction with a liquid Ar cooled trap which condenses unreacted $N_2O$. The measurement is completed when no further $N_2$ is evolved. The amount of $N_2O$ consumed and $N_2$ evolved is assumed to follow the reaction chemistry $N_2O+2Cu \rightarrow N_2+Cu_2O$ on the surface of the reduced catalyst; the reaction does occur in the bulk (i.e., subsurface) Cu layers. The Cu dispersion is then calculated by taking the ratio of surface Cu atoms per gram catalyst measured by this method (i.e. atoms $N_2$ evolved multiplied by 2) divided by the total number of Cu atoms per gram catalyst.

In any of the above embodiments, the mixed metal oxide may include Cu and Mn. In any of the above embodiments, the mixed metal oxide may include Cu and Mn, and the catalyst may include about 2 wt % to about 10 wt % Mn. The amount of Mn in the catalyst may be about 2 wt %, about 3 wt %, about 4 wt %, about 5 wt %, about 6 wt %, about 7 wt %, about 8 wt %, about 9 wt %, about 10 wt %, or any range including and in between any two of these values. For example, in any of the embodiments described herein the mixed metal oxide may include Cu and Mn, and the catalyst may include about 2 wt % to about 6 wt % Mn.

In any of the above embodiments, the mixed metal oxide may include Cu and Zn. In any of the above embodiments, the mixed metal oxide may include Cu and Zn, and the catalyst may include about 15 wt % to about 50 wt % Zn. The amount of Zn in the catalyst may be about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 47 wt %, about 48 wt %, about 49 wt %, about 50 wt %, or any range including and in between any two of these values. For example, the catalyst may include about 15 wt % to about 25 wt % Zn.

The amount of the alumina in the catalyst may be from about 10 wt % to about 30 wt %. The amount of the alumina in the catalyst may be about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, or any range including and in between any two of these values. For example, the amount of the alumina in the catalyst may be about 15 wt % to about 25 wt %.

The amount of the silica in the catalyst may be from about 10 wt % to about 30 wt %. The amount of the silica in the catalyst may be about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, or any range including and in between any two of these values. For example, the amount of the silica in the catalyst may be about 15 wt % to about 25 wt %.

The amount of the calcium in the catalyst may be from about 2 wt % to about 10 wt %. The amount of calcium in the catalyst may be about 2 wt %, about 3 wt %, about 4 wt %, about 5 wt %, about 6 wt %, about 7 wt %, about 8 wt %, about 9 wt %, about 10 wt %, or any range including and in between any two of these values. For example, it may be that in any of the embodiments described herein that the amount of calcium in the catalyst is from about 3 wt % to about 8 wt %.

The catalyst may be substantially free of sodium. In any of the above embodiments, the amount of sodium in the catalyst may be less than about 0.4 wt %, less than about 0.3 wt %, less than about 0.2 wt %, less than about 0.1 wt %, or any range including and in between any two of these values. In any of the above embodiments, the catalyst may be substantially free of chromium. In any of the above embodiments, the amount of chromium in the catalyst may be less than about 0.4 wt %, less than about 0.3 wt %, less than about 0.2 wt %, less than about 0.1 wt %, or any range including and in between any two of these values. In any of the above embodiments, the catalyst may be substantially free of barium. In any of the above embodiments, the amount of barium in the catalyst may be less than about 0.4 wt %, less than about 0.3 wt %, less than about 0.2 wt %, less than about 0.1 wt %, or any range including and in between any two of these values.

The catalyst may have a Brunauer-Emmett-Teller surface area ("BET surface area") from about 10 $m^2$/g to about 150 $m^2$/g. The BET surface area may be determined by several methods, including the method described in ASTM-D3663-03 (2008), incorporated herein by reference in its entirety for any and all purposes. The BET surface area may be about 10 $m^2$/g, about 12 $m^2$/g, about 14 $m^2$/g, about 16 $m^2$/g, about 18 $m^2$/g, about 20 $m^2$/g, about 22 $m^2$/g, about 24 $m^2$/g, about 26 $m^2$/g, about 28 $m^2$/g, about 30 $m^2$/g, about 32 $m^2$/g, about 34 $m^2$/g, about 36 $m^2$/g, about 38 $m^2$/g, about 40 $m^2$/g, about 42 m²/g, about 44 m²/g, about 46 m²/g, about 48 m²/g, about 50 m²/g, about 52 m²/g, about 54 m²/g, about 56 m²/g, about 58 m²/g, about 60 m²/g, about 62 m²/g, about 64 m²/g, about 66 m²/g, about 68 m²/g, about 70 m²/g, about 72 m²/g, about 74 m²/g, about 76 m²/g, about 78 m²/g, about 80 m²/g, about 82 m²/g, about 84 m²/g, about 86 m²/g, about 88 m²/g, about 90 m²/g, about 92 m²/g, about 94 m²/g, about 96 m²/g, about 98 m²/g, about 100 m²/g, about 102 m²/g, about 104 m²/g, about 106 m²/g, about 108 m²/g, about 110 m²/g, about 112 m²/g, about 114 m²/g, about 116 m²/g, about 118 m²/g, about 120 m²/g, about 122 m²/g, about 124 m²/g, about 126 m²/g, about 128 m²/g, about 130 m²/g, about 132 m²/g, about 134 m²/g, about 136 m²/g, about 138 m²/g, about 140 m²/g, about 142 m²/g, about 144 m²/g, about 146 m²/g, about 148 m²/g, about 150 m²/g, or any range including and in between any two of these values. For example, in any of the above embodiments, the catalyst may have a BET surface area from about 10 m²/g to about 70 m²/g.

The catalyst may have a mercury pore volume from about 0.10 cm³/g to about 0.80 cm³/g. The mercury pore volume may be determined by a variety of methods, including, but are not limited to, the method described in ASTM-D4284-12, incorporated herein by reference in its entirety for any and all purposes. The mercury pore volume may be about 0.10 cm³/g, about 0.15 cm³/g, about 0.20 cm³/g, about 0.25 cm³/g, about 0.30 cm³/g, about 0.35 cm³/g, about 0.40 cm³/g, about 0.45 cm³/g, about 0.50 cm³/g, about 0.55 cm³/g, about 0.60 cm³/g, about 0.65 cm³/g, about 0.70 cm³/g, about 0.75 cm³/g, about 0.80 cm³/g, or any range including and in between any two of these values.

The catalyst may have a packed ambient bulk density from about 0.3 g/cm³ to about 1.6 g/cm³. The packed ambient bulk density may be determined by a variety of methods, including, but are not limited to, the method described in ASTM-D4164-82, incorporated herein by reference in its entirety for any and all purposes. The packed ambient bulk density may be about 0.3, about 0.4 g/cm³, about 0.5 g/cm³, about 0.6 g/cm³, about 0.7 g/cm³, about 0.8 g/cm³, about 0.9 g/cm³, about 1.0 g/cm³, about 1.1 g/cm³, about 1.2 g/cm³, about 1.3 g/cm³, about 1.4 g/cm³, about 1.5 g/cm³, about 1.6 g/cm³, or any range including and in between any two of these values.

The catalyst may have a side crush strength from about 2.5 lbs/mm to about 12 lbs/mm. Side crush strength may be determined according to ASTM-04179-82, incorporated herein by reference in its entirety for any and all purposes, as well as other methods well-known to one of skill in the art. The side crush strength may be about 2.5 lbs/mm, about 3.0 lbs/mm, about 3.5 lbs/mm, about 4.0 lbs/mm, about 4.5 lbs/mm, about 5.0 lbs/mm, about 5.5 lbs/mm, about 6.0 lbs/mm, about 6.5 lbs/mm, about 7.0 lbs/mm, about 7.5 lbs/mm, about 8.0 lbs/mm, about 8.5 lbs/mm, about 9.0 lbs/mm, about 9.5 lbs/mm, about 10.0 lbs/mm, about 10.5 lbs/mm, about 11.0 lbs/mm, about 11.5 lbs/mm, about 12 lbs/mm, or any range including and in between any two of these values.

The catalyst may be in a shape that includes at least one of cylindrical, tubular, polylobular, fluted, or ridged. In any of the above embodiments, the catalyst may have a diameter from about 0.5 mm to about 3.0 mm. The diameter of the catalyst may be about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, or any range including and in between any two of these values. For example, it may be that the catalyst has a diameter from about 1.0 mm to about 2.0 mm.

In another aspect, a method of making any of the above catalysts is provided, where the process includes calcining a shaped material. The shaped material is formed by shaping a paste. The paste of the method includes a Cu oxide and at least one metal oxide of Mn, Zn, Ni, or Co; an alumina; a silica sol; and calcium hydroxide. The calcium hydroxide may arise from combining precursors, such as a calcium salt and a hydroxide source. It is also contemplated the metal oxide of the process may arise from a precursor that provides the metal oxide. Such precursors include, but not limited, to carbonates and nitrates of the metals. In any of the above embodiments, it may be the Cu oxide includes cupric oxide.

The paste may further include a clay material, such as, but not limited to, an alumina-silicate clay. Alumina-silicate clays include, but are not limited to, attapulgites, sepiolites, serpentines, kaolinites, calcium montmorillonites, and mixtures of any two or more thereof. Such alumina-silicate clays may include clays obtained from the Meigs-Attapulgus-Quincy fullers earth districts, located in southwest Georgia and northern Florida. The term "attapulgite" is used to refer to chain lattice type clay minerals, encompassing minerals and mineral groups variously referred to by those skilled in the art as "attapulgite," "palygorskite," "sepiolite," and "hormite." In any of the above embodiments, the clay material includes attapulgite. In any of the above embodiments, the attapulgite is present as the largest component by mass of the clay material. The clay material may be undried, dried, or calcined. It may be the free moisture content of the clay material is from about 3 wt % to about 8 wt % of the clay material, where "free-moisture content" refers to the amount of water removed from the clay material by heating at about 105° C. (220° F.) until a constant weight is maintained. In any of the above embodiments of the process, the clay material may be powdered. In any of the above embodiments, the clay material may be powdered and have mesh size less than about 200 mesh (U.S. Standard). In any of the above embodiments, the clay material may be powdered and have mesh size less than about 325 mesh (U.S. Standard).

In any embodiment of the methods described herein, the paste may further include a solvent. The solvent may include water, an alcohol (e.g., methanol, ethanol, propanol), a ketone (e.g., acetone, methyl ethyl ketone), an aldehyde (e.g., propanol, butanal), or a mixture of any two or more thereof. In any of the above embodiments, the solvent may include water. The amount of solvent used is an amount that provides a consistency which allows for a shape to be formed out of the paste, but not so fluid as to fail to hold the formed shape. Typically, the total amount of solvent in the paste, including that contributed by other components (e.g., water from a clay) is from about 15 wt % to about 60% by weight of the paste. The total amount of solvent in the paste may be about 15 wt %, about 16 wt %, about 17 wt %, about 18 wt %, about 19 wt %, about 20 wt %, about 22 wt %, about 24 wt %, about 26 wt %, about 28 wt %, about 30 wt %, about 32 wt %, about 34 wt %, about 36 wt %, about 38 wt %, about 40 wt %, about 42 wt %, about 44 wt %, about 46 wt %, about 48 wt %, about 50 wt %, about 52 wt %, about 54 wt %, about 56 wt %, about 58 wt %, about 60 wt %, or any range including and in between any two of these values. In any of the above embodiments of the method, it may be that the total amount of solvent is from about 35 wt % to about 55 wt % of the paste.

In any of the above embodiments, the shaped material may be prepared by tableting or extruding the paste. In any of the above embodiments, the shape may include at least one of cylindrical, tubular, polylobular, fluted, or ridged. In any of the above embodiments, it may be the paste includes a rheology control agent and/or a pore forming agent. Rheology control agents include, but are not limited to, starches, sugars, glycols, polyols, powdered organic polymers, graphite, stearic acid and its esters. Pore forming agents include, but are not limited to, graphite, polypropylene or other organic polymer powders, activated carbon, charcoal, sugars, starches and cellulose flour. The rheology control agent and/or pore forming agent may be present in an amount of from about 0.5 wt % to about 20 wt % of the paste. In any of the above embodiments, it may be the rheology control agent is an extrusion aid. In any of the above embodiments, it may be the extrusion aid includes a polysaccharide.

The calcining may include heating at a temperature from about 300° C. to about 1,000° C. The calcining temperature may be about 300° C., about 350° C., about 400° C., about 450° C., about 500° C., about 550° C., about 600° C., about 650° C., about 700° C., about 750° C., about 800° C., about 850° C., about 900° C., about 950° C., about 1,000° C., or any range including and in between any two of these values. In any of the above embodiments, it may be the duration of the calcining step is about 15 minutes to about 12 hours. The duration of the calcining step may be about 15 minutes, about 30 minutes, about 45 minutes, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 7 hours, about 8 hours, about 9 hours, about 10 hours, about 11 hours, about 12 hours, or any range including and in between any two of these values. In any of the above embodiments, it may be the shaped material is dried prior to calcining. In any of the above embodiments, it may be the shaped material is dried at a temperature from about 40° C. to about 250° C. The shaped material may be dried at a temperature of about 40° C., about 50° C., about 60° C., about 70° C., about 80° C., about 90° C., about 100° C., about 125° C., about 150° C., about 175° C., about 200° C., about 225° C., about 250° C., or any range including and in between any two of these values.

In another aspect, a process is provided for hydrogenation and/or hydrogenolysis of a feedstock by contacting the feedstock and $H_2$ and any of the above catalysts, wherein the feedstock includes at least one carbonyl group. In many embodiments, the process may include hydrogenolysis of the feedstock. Feedstocks are compounds with at least one carbonyl group (such as ketones, aldehydes, esters, and carboxylic acids). The feedstock may also include one or more other functional groups that contain one or more π bonds, such as a carbon-carbon double bond, a carbon-carbon triple bond, a carbon-heteroatom double bond, or a carbon-heteroatom triple bond. Functional groups containing a π bond include, but are not limited to, alkenes, alkynes, carbonyls, nitro groups, and nitriles. Feedstocks therefore include, but are not limited to, free fatty acids, fatty acid esters (including mono-, di-, and triglycerides), or combinations thereof. In any of the above embodiments, it may be the fatty acid ester includes a fatty acid methyl ester, a fatty acid ethyl ester, a fatty acid propyl ester, a fatty acid butyl ester, or mixtures of any two or more thereof. The free fatty acids, fatty acid esters, or combinations thereof may be derived from animal fats, animal oils, plant fats, plant oils, vegetable fats, vegetable oils, or mixtures of any two or more thereof. Plant and/or vegetable oils include, but are not limited to, soybean oil, canola oil, coconut oil, rapeseed oil, tall oil, tall oil fatty acid, palm oil, palm oil fatty acid distillate, palm kernel oil, jatropha oil, sunflower oil, castor oil, camelina oil, algae oil, seaweed oil, oils from halophiles, and mixtures of any two or more thereof. Animal fats and/or oils as used above includes, but is not limited to, inedible tallow, edible tallow, technical tallow, floatation tallow, lard, poultry fat, poultry oils, fish fat, fish oils, and mixtures of any two or more thereof. In any of the above embodiments of the process, the free fatty acids, fatty acid esters, or combinations thereof include a hydrogenated animal fat, animal oil, plant fat, plant oil, vegetable fat, vegetable oil, or mixture of any two or more thereof. In any of the above embodiments, the feedstock may include fatty acid methyl esters. Such fatty acid methyl esters may be formed by esterification of free fatty acids with methanol or transesterification of fatty acid esters with methanol. In any of the above embodiments, it may be the feedstock includes free fatty acids. The free fatty acids may be from about 0.1 wt % to about 10 wt % of the feedstock. Therefore, the amount of free fatty acids in the feedstock may be about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1.0 wt %, about 1.2 wt %, about 1.4 wt %, about 1.6 wt %, about 1.8 wt %, about 2.0 wt %, about 2.2 wt %, about 2.4 wt %, about 2.6 wt %, about 2.8 wt %, about 3.0 wt %, about 3.2 wt %, about 3.4 wt %, about 3.6 wt %, about 3.8 wt %, about 4.0 wt %, about 4.2 wt %, about 4.4 wt %, about 4.6 wt %, about 4.8 wt %, about 5.0 wt %, about 5.5 wt %, about 6.0 wt %, about 6.5 wt %, about 7.0 wt %, about 7.5 wt %, about 8.0 wt %, about 8.5 wt %, about 9.0 wt %, about 10.0 wt %, or any range including and in between any two of these values.

In any of the above embodiments, the feedstock includes compounds where the longest carbon chain has a carbon number from $C_8$-$C_{18}$. Thus, the feedstock may include a compound where the longest carbon chain has a carbon number of $C_8$, $C_9$, $C_{10}$, $C_{11}$, $C_{12}$, $C_{13}$, $C_{14}$, $C_{15}$, $C_{16}$, $C_{17}$, $C_{18}$, or any range including and in between any two of these values. In any of the above embodiments, the feedstock may include a compound where the longest carbon chain has with a carbon number of $C_{12}$-$C_{18}$. In any of the above embodiments, the feedstock may include fatty acid methyl esters where the longest carbon chain has a carbon number from $C_5$-$C_{18}$. In any of the above embodiments, it may be the feedstock includes at least one of methyl laurate, methyl myristate, methyl palmitate, or methyl stearate. In any of the above embodiments, it may be the process involves producing a fatty alcohol. The fatty alcohol may have a carbon number from $C_8$-$C_{18}$. Thus, the fatty alcohol may have a carbon number of $C_8$, $C_9$, $C_{10}$, $C_{11}$, $C_{12}$, $C_{13}$, $C_{14}$, $C_{15}$, $C_{16}$, $C_{17}$, $C_{18}$, or include fatty alcohols with a carbon number including and in between any two of these values.

The molar ratio of the $H_2$ to the feedstock may be from about 100:1 to about 2000:1. In any of the above embodiments, the hydrogenation and/or hydrogenolysis may occur at a temperature from about 100° C. to about 350° C. The temperature of the process may be about 100° C., about 150° C., about 200° C., about 250° C., about 300° C., about 350° C., or any range including or in between any two of these values. In any of the above embodiments, the hydrogenation and/or hydrogenolysis may occur at a pressure from about 1 bar to about 60 bar. The hydrogenation and/or hydrogenolysis pressure may be independent from each other, and may be about 1 bar, about 2 bar, about 3 bar, about 4 bar, about 5 bar, about 6 bar, about 7 bar, about 8 bar, about 9 bar, about 10 bar, about 12 bar, about 14 bar, about 16 bar, about 18 bar, about 20 bar, about 22 bar, about 24 bar, about 26 bar, about 28 bar, about 30 bar, about 32 bar, about 34 bar, about 36 bar, about 38 bar, about 40 bar, about 42 bar, about 44 bar, about 46 bar, about 48 bar, about 50 bar, about 52 bar, about 54 bar, about 56 bar, about 58 bar, about 60 bar, or any range including and in between any two of these values. In any of the above embodiments, contacting the feedstock and $H_2$ with the catalyst of the present technology may involve flowing the feedstock and $H_2$ at a liquid hourly space velocity ("LHSV") of about 0.1 $hr^{-1}$ to about 10.0 $hr^{-1}$. The LHSV may be about 0.1 $hr^{-1}$, about 0.2 $hr^{-1}$, about 0.3 $hr^{-1}$, about 0.4 $hr^{-1}$, about 0.5 $hr^{-1}$, about 0.6 $hr^{-1}$, about 0.7 $hr^{-1}$, about 0.8 $hr^{-1}$, about 0.9 $hr^{-1}$, about 1.0 $hr^{-1}$, about 1.2 $hr^{-1}$, about 1.4 $hr^{-1}$, about 1.6 $hr^{-1}$, about 1.8 $hr^{-1}$, about 2.0 $hr^{-1}$, about 2.2 $hr^{-1}$, about 2.4 $hr^{-1}$, about 2.6 $hr^{-1}$, about 2.8 $hr^{-1}$, about 3.0 $hr^{-1}$, about 3.2 $hr^{-1}$, about 3.4 $hr^{-1}$, about 3.6 $hr^{-1}$, about 3.8 $hr^{-1}$, about 4.0 $hr^{-1}$, about 4.2 $hr^{-1}$, about 4.4 $hr^{-1}$, about 4.6 $hr^{-1}$, about 4.8 $hr^{-1}$, about 5.0 $hr^{-1}$, about 5.5 $hr^{-1}$, about 6.0 $hr^{-1}$, about 6.5 $hr^{-1}$, about 7.0 $hr^{-1}$, about 7.5 $hr^{-1}$, about 8.0 $hr^{-1}$, about 8.5 $hr^{-1}$, about 9.0 $hr^{-1}$, about 10.0 $hr^{-1}$, or any range including and in between any two of these values.

The process may include contacting the catalyst with $H_2$ prior to contacting the feedstock and $H_2$. Contacting the catalyst with $H_2$ prior to contacting the feedstock and $H_2$ may include any one or more of the temperatures, pressures, or LSHVs previously described.

The examples herein are provided to illustrate advantages of the present technology and to further assist a person of ordinary skill in the art with preparing or using the present technology. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

Preparation of Catalysts. The catalysts were prepare by wet-mixing of mixed metal oxide powders with calcium hydroxide, Attagel-30 clay and Nalco or Akzo silica sol using a Littleford plow mixer. Zusoplast PS-1, a polysaccharide extrusion aid, was also included in the wet mix. The composition of the mixed metal oxide powders was as follows: the CuMn powder was 60 wt % CuO, 30 wt % $Al_2O_3$, and 10 wt % $MnO_2$; the CuZn powder was 36 wt % CuO, 26 wt % $Al_2O_3$, and 38 wt % ZnO. Table 1 provides the added components and respective weights (in grams) for generating each catalyst wet mix.

TABLE 1

| | Wet Mix for CuMn-1 | Wet Mix for CuMn-2 | Wet Mix for CuZn-1 |
| --- | --- | --- | --- |
| CuMn powder (calcined at 650° C.) | 500 | | |
| CuMn powder (calcined at 800° C.) | | 500 | |
| CuZn powder (calcined at 600° C.) | | | 500 |
| Calcium hydroxide | 71 | 71 | 71 |
| Attagel 30 clay | 73 | 73 | 73 |
| Zusoplast PS 1 | 29 | 29 | 29 |
| Silica sol | 265 | 265 | 265 |
| $H_2O$ (deionized) | 265 | 235 | 235 |

In each case, the wet-mix was extruded through a 1 inch diameter die with a trilobe shape. Each extrudate was then calcined, providing catalysts with a diameter of about 1.5 millimeters.

Composition of Exemplary Catalysts and a Comparative CuCrMn Catalyst. The compositions and properties of the resulting CuMn-1, CuMn-2, and CuZn-1 catalysts are provided in Table 2 below, as measured by ICP/AES and XRF (limit of detection about 0.1 wt %). A 1.5 mm diameter CuCrMn extrudate (CuCrMn catalyst) was also prepared as a comparative example.

TABLE 2

| | CuMn-1 | CuMn-2 | CuZn-1 | CuCrMn (comparative) |
| --- | --- | --- | --- | --- |
| CuO (wt %) | 42 | 39 | 25 | 39 |
| $Cr_2O_3$ (wt %) | N.D. | N.D. | N.D. | 33 |
| $MnO_2$ (wt %) | 7 | 8 | N.D. | 4 |
| $ZnO_2$ (wt %) | N.D. | N.D. | 27 | N.D. |
| $Al_2O_3$ (wt %) | 21 | 21 | 18 | |
| $SiO_2$ (wt %) | 19 | 19 | 21 | 19 |
| CaO (wt %) | 8 | 8 | 8 | |
| $Na_2O$ (wt %) | N.D. | N.D. | N.D. | N.D. |
| Cu dispersion (%) | 1.4 | not measured | not measured | not measured |
| % Loss on ignition | 0.8 | not measured | not measured | not measured |
| BET surface area ($m^2/g$) | 16 | 48 | 22 | 46 |
| Hg pore volume [10-10k A] (cc/g) | 0.26 | 0.60 | not measured | 0.36 |
| Packed ambient bulk density (g/cc) | 0.80 | 0.77 | 0.88 | 0.94 |
| Side Crush Strength (lbs/mm) | 4.5 | 3.6 | 2.8 | 2 |

N.D. = Not Detected

Sodium (as $Na_2O$) was not detected, therefore, the level of sodium in the compositions is less than about 0.1 wt % and may be even lower. Similarly, other compounds may be present in amounts less than about 0.1 wt %.

Hydrogenolysis of a $C_{12}$-$C_{14}$ fatty acid methyl ester ($C_{16}$-$C_{18}$ FAME) feed with CuMn-1 and a comparative CuCrMn catalyst. Hydrogenolysis of $C_{12}$-$C_{14}$ fatty acid methyl ester ($C_{12}$-$C_{14}$ FAME) feed with CuMn-1 and the comparative CuCrMn catalyst. CuMn-1 and comparative CuCrMn were evaluated for the hydrogenolysis of a $C_{12}$-$C_{14}$ fatty acid methyl ester ($C_{12}$-$C_{14}$ FAME) feed in a fixed bed reactor using the conditions indicated in FIG. 1 and a $H_2$/feed molar ratio of 250:1. The $C_{12}$-$C_{14}$ FAME feed exhibited an acid number of 0.5 (AN=0.6), thus indicating a free fatty acid content of 0.0005 wt %. FIG. 1 shows that the CuMn-1 of the present technology has a much greater activity throughout the entire course of the reaction. Notably, even with the normal feed, the comparative CuCrMn catalyst shows a reduction in activity during the first 100 hours. Accelerated aging of each catalyst was accomplished by spiking the $C_{12}$-$C_{14}$ FAME feed with a saturated linear $C_{12}$ free fatty acid (n-dodecanoic acid, common name: lauric acid), namely a 0.5 wt % $C_{12}$ FFA spike from 100 hours to 300 hours on stream, and a 1 wt % $C_{12}$ FFA spike from 450 hours to 500 hours. FIG. 1 shows that the CuMn-1 of the present technology has a slight reduction of activity during the 0.5 wt % $C_{12}$ FFA spike and about a 10% reduction during the 1 wt % $C_{12}$ FFA spike, but each of these impacts reverses to about the initial activity upon discontinuing the $C_{12}$ FFA spike. At hour 500, the flow rate is reduced to an LHSV of 0.65 $hr^{-1}$ whereupon the CuMn-1 of the present technology continues to perform at high conversion until the end of run. No irreversible deactivation is observable after a total of 700 hours on stream with two n-$C_{12}$ FFA spikes. In contrast, FIG. 1 shows the activity of the comparative CuCrMn catalyst is significantly reduced by the 0.5 wt % $C_{12}$ FFA spike, and upon discontinuing the 0.5 wt % $C_{12}$ FFA spike the CuCrMn catalyst is shown to exhibit significant irreversible deactivation.

Figure 2:
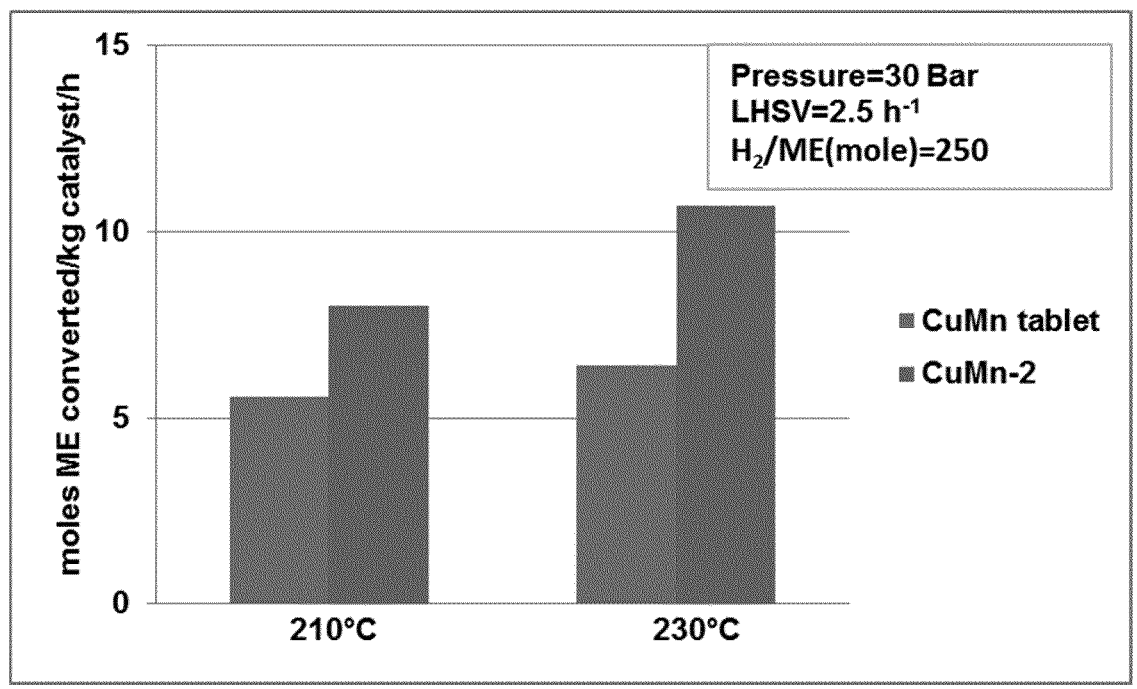
FIG. 2 illustrates the hydrogenolysis productivity per kilogram of one embodiment of a catalyst of the present technology for a $C_{12}$-$C_{14}$ FAME feed in comparison to a tabletted CuMn catalyst, according to the working examples.

CuMn-2 was evaluated against a 3 mm diameter tabletted CuMn catalyst ("CuMn tablet") for the hydrogenolysis of a $C_{12}$-$C_{14}$ FAME feed in a fixed bed reactor using the conditions indicated in FIG. 2. FIG. 2 provides the results of the reaction at 210° C. and 230° C., where the productivity (the moles $C_{12}$-$C_{14}$ FAME feed converted per kilogram catalyst per hour) of the CuMn-2 catalyst of the present technology is about 40% higher than the comparative CuMn tablet at 210° C. and almost 100% higher than the comparative CuMn tablet at 210° C. Without being bound by theory, it is believed that the higher productivity is due not only to the higher activity of the catalysts of the present technology (as shown in FIG. 1) but also the lower packed ambient bulk density of the catalysts of the present technology. Thus, the catalysts of the present technology not only exhibit longer life but also offer a cost advantage due to the lower packed ambient bulk density.

Figure 3:
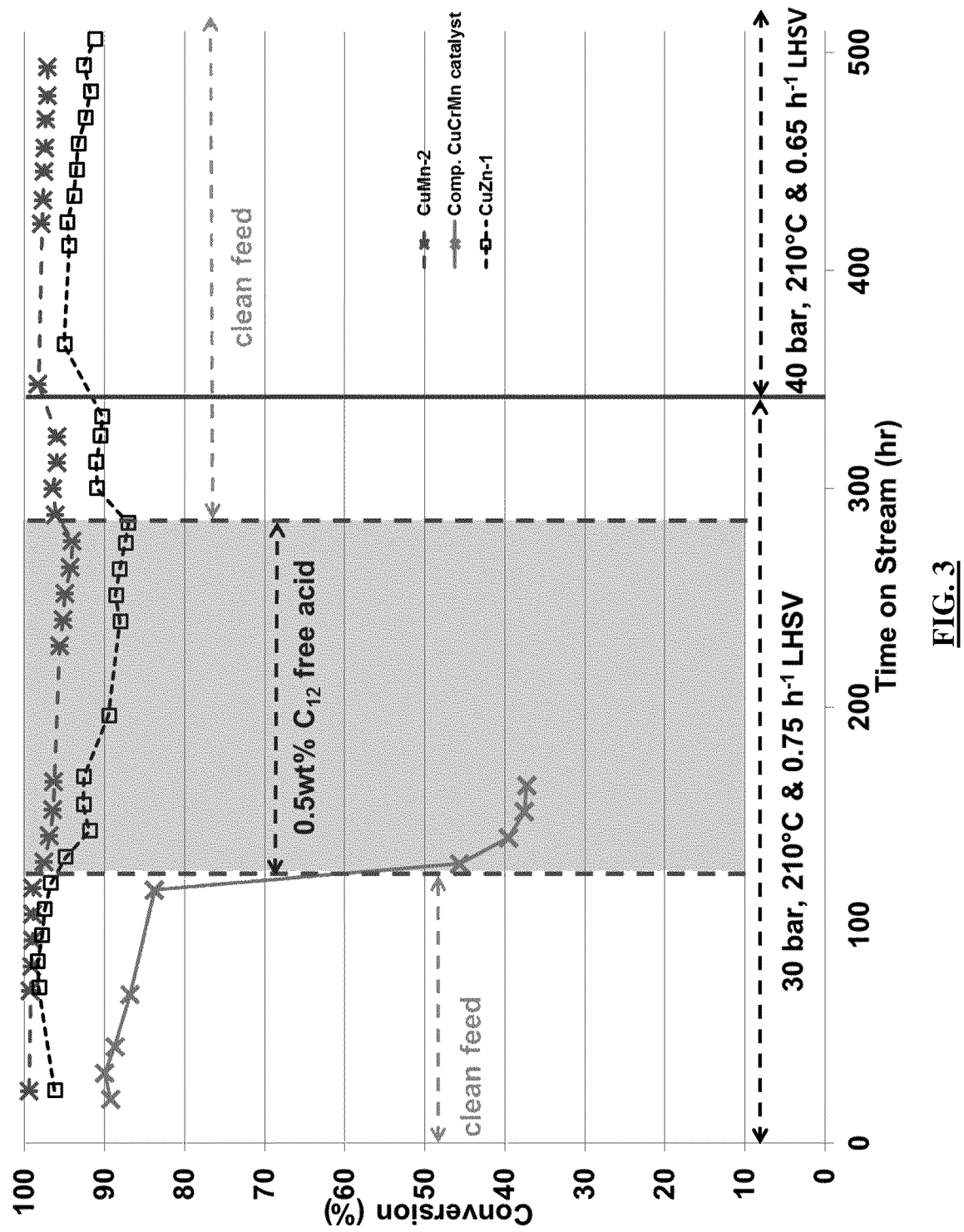
FIG. 3 illustrates the hydrogenolysis performance of two embodiments of catalysts of the present technology for a $C_{16}$-$C_{18}$ fatty acid methyl ester ($C_{16}$-$C_{18}$ FAME) feed in comparison to a CuCrMn catalyst, according to the working examples.

Hydrogenolysis of a $C_{16}$-$C_{18}$ fatty acid methyl ester ($C_{16}$-$C_{18}$ FAME) feed with CuMn-2, CuZn-1, and comparative CuCrMn catalysts. CuMn-2, CuZn-1, and the comparative CuCrMn catalyst of Table 2 were evaluated for the hydrogenolysis of a $C_{16}$-$C_{18}$ fatty acid methyl ester ($C_{16}$-$C_{18}$ FAME) feed in a fixed bed reactor using the conditions indicated in FIG. 3 and a $H_2$/feed molar ratio of 1000:1. The $C_{16}$-$C_{18}$ FAME feed exhibited an acid number of 0.6 (AN=0.6), thus indicating a free fatty acid content of 0.0006 wt %. FIG. 3 shows that CuMn-2 and CuZn-1 have a higher activity than the CuCrMn catalyst for the $C_{16}$-$C_{18}$ FAME feed. The CuCrMn catalyst also exhibits a noticeable reduction in activity during the first 120 hours with the $C_{16}$-$C_{18}$ FAME feed.

Upon performing an accelerated aging experiment by spiking the $C_{16}$-$C_{18}$ FAME feed with 0.5 wt % n-Cu FFA, CuMn-2 and CuZn-1 exhibit a small reduction in conversion over the next 160 hours. This small reduction in conversion rebounds upon discontinuing the 0.5 wt % n-Cu FFA, indicating the small reduction in conversion was reversible for the CuMn-2 and CuZn-1 catalysts. CuMn-2 was maintained at the same conditions as upon startup (pressure of 30 bar, a temperature of 210° C., LHSV of 0.75 $hr^{-1}$) and continued to perform at high conversion until the end of run. Thus, after a total of 500 hours on stream that included a 160 hour 0.5 wt % n-Cu FFA spike, no irreversible deactivation is observable. In regard to CuZn-1, at hour 340 the flow rate is reduced to an LHSV of 0.65 $hr^{-1}$ and the pressure increased to 40 bar whereupon CuZn-1 continue to perform at high conversion until the end of run. At the end of the run, after a total of 500 hours on stream that included a 160 hour 0.5 wt % n-Cu FFA spike, no irreversible deactivation is observable for CuZn-1. In contrast to both CuMn-2 and CuZn-1, the CuCrMn catalyst experiences a precipitous decline in conversion upon introduction of the 0.5 wt % n-Cu FFA spike.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A catalyst comprising:
a mixed metal oxide comprising Cu and Mn;
an alumina;
silica; and
calcium;
wherein the catalyst comprises about 2 wt % to about 10 wt % Mn.

2. The catalyst of claim 1, wherein the catalyst comprises a surface, and wherein the percent of Cu at the surface in relation to total Cu content of the catalyst is from about 0.5% to about 20%.

3. The catalyst of claim 1, wherein the catalyst comprises about 15 wt % to about 50 wt % Cu.

4. The catalyst of claim 1, wherein the mixed metal oxide further comprises Zn, and wherein the catalyst comprises about 15 wt % to about 50 wt % Zn.

5. The catalyst of claim 1, wherein the alumina is present in the catalyst at about 10 wt % to about 30 wt %.

6. The catalyst of claim 1, wherein the silica is present in the catalyst at about 10 wt % to about 30 wt %.

7. The catalyst of claim 1, wherein the calcium is present in the catalyst at about 2 wt % to about 10 wt %.

8. The catalyst of claim 1, wherein the catalyst comprises 0.5 wt % or less of sodium, chromium, barium, or a combination of two or more thereof.

9. The catalyst of claim 1, wherein the catalyst has a Brunauer-Emmett-Teller surface area from about 10 $m^2/g$ to about 150 $m^2/g$.

10. The catalyst of claim 1, wherein the catalyst has a mercury pore volume from about 0.10 $cm^3/g$ to about 0.80 $cm^3/g$.

11. The catalyst of claim 1, wherein the catalyst has a packed ambient bulk density from about 0.3 g/cm3 to about 1.6 $g/cm^3$.

12. The catalyst of claim 1, wherein the catalyst has a side crush strength from about 2.5 lbs/mm to about 12 lbs/mm.

13. A method of making the catalyst of claim 1, the method comprising calcining a shaped material;
wherein:
the shaped material is formed by shaping a paste, the paste comprising:
a mixed metal oxide comprising Cu and Mn;
an alumina;
a silica sol; and
calcium hydroxide.

14. A process comprising
hydrogenation and/or hydrogenolysis of a feedstock by contacting the feedstock and $H_2$ with the catalyst of claim 1,
wherein the feedstock comprises at least one carbonyl group.

15. The process of claim 14, wherein the feedstock comprises fatty acid methyl esters.

* * * * *